(12) United States Patent
Kane et al.

(10) Patent No.: US 8,290,592 B2
(45) Date of Patent: Oct. 16, 2012

(54) IMPLANTABLE MEDICAL DEVICE HEADER WITH OPTICAL INTERFACE

(75) Inventors: Michael John Kane, Lake Elmo, MN (US); Greg Paul Carpenter, Centerville, MN (US); Amy Christine Kubas, Hugo, MN (US); Jennifer Lynn Pavlovic, Afton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/533,948

(22) Filed: Sep. 21, 2006

(65) Prior Publication Data

US 2008/0077190 A1    Mar. 27, 2008

(51) Int. Cl.
*A61N 1/00* (2006.01)
(52) U.S. Cl. .............................. 607/36; 607/37; 607/122
(58) Field of Classification Search .............. 607/36–37, 607/122
See application file for complete search history.

(56) References Cited

U.S. PATENT DOCUMENTS

| | | | |
|---|---|---|---|
| 5,454,837 A | 10/1995 | Lindegren et al. | |
| 5,490,323 A | 2/1996 | Thacker et al. | |
| 5,520,190 A | 5/1996 | Benedict et al. | |
| 5,556,421 A | 9/1996 | Prutchi et al. | |
| 5,562,716 A * | 10/1996 | Kuzma | 607/36 |
| 5,730,125 A | 3/1998 | Prutchi et al. | |
| 5,902,326 A * | 5/1999 | Lessar et al. | 607/36 |
| 6,112,121 A * | 8/2000 | Paul et al. | 607/37 |
| 6,169,925 B1 * | 1/2001 | Villaseca et al. | 607/60 |
| 6,416,334 B1 * | 7/2002 | Plishner | 439/75 |
| 6,491,639 B1 | 12/2002 | Turcott | |
| 6,711,440 B2 | 3/2004 | Deal et al. | |
| 6,718,207 B2 | 4/2004 | Connelly | |
| 6,725,092 B2 | 4/2004 | MacDonald et al. | |
| 6,832,115 B2 | 12/2004 | Borkan | |
| 6,859,667 B2 | 2/2005 | Goode | |

(Continued)

FOREIGN PATENT DOCUMENTS

WO    WO 00/09012    2/2000

OTHER PUBLICATIONS

"Cardiac defibrillators—Connector assembly DF-1 for implantable defibrillators—Dimensions and test requirements", *ISO 11318, Second edition*, (Aug. 1, 2002),pp. 1-27.

(Continued)

*Primary Examiner* — Nicole F Lavert
(74) *Attorney, Agent, or Firm* — Pauly, DeVries, Smith & Deffner, L.L.C.

(57) ABSTRACT

Disclosed herein, among other things, is an implantable medical device header assembly with an optical interface. The header assembly can include a housing defining a cavity; an electrical contact disposed along the cavity; an electrical conductor configured to electrically couple the electrical contact with the implantable medical device; and an optical conductor. The header assembly can include a housing defining a first cavity for receiving a proximal end of an electrical lead; and a second cavity for receiving a proximal end of an optical lead. The header assembly can include a housing configured to be coupled to the implantable medical device, the housing defining a lead port for receiving a proximal end of a lead, the port configured to be in electrical and optical communication with the lead; a transducer disposed within the housing, and an electrical conductor disposed within the housing. Other aspects and embodiments are provided herein.

16 Claims, 8 Drawing Sheets

U.S. PATENT DOCUMENTS

| | | |
|---|---|---|
| 6,968,235 B2 * | 11/2005 | Belden et al. .................. 607/60 |
| 7,020,517 B2 | 3/2006 | Weiner |
| 7,076,292 B2 | 7/2006 | Forsberg |
| 7,190,993 B2 * | 3/2007 | Sharma et al. ................ 600/510 |
| 7,349,618 B2 | 3/2008 | Nielsen et al. |
| 7,395,118 B2 * | 7/2008 | Erickson ....................... 607/116 |
| 2002/0138113 A1 | 9/2002 | Connelly et al. |
| 2002/0156512 A1 | 10/2002 | Borkan |
| 2002/0183796 A1 | 12/2002 | Connelly |
| 2003/0018364 A1 * | 1/2003 | Belden et al. .................. 607/37 |
| 2003/0130700 A1 | 7/2003 | Miller et al. |
| 2003/0130701 A1 | 7/2003 | Miller |
| 2003/0195577 A1 | 10/2003 | Pigott |
| 2003/0204217 A1 | 10/2003 | Greatbatch |
| 2003/0204220 A1 | 10/2003 | Forsberg |
| 2004/0082986 A1 | 4/2004 | Westlund et al. |
| 2004/0220629 A1 | 11/2004 | Kamath et al. |
| 2005/0070987 A1 * | 3/2005 | Erickson ....................... 607/122 |
| 2005/0096720 A1 * | 5/2005 | Sharma et al. ................ 607/122 |
| 2005/0165456 A1 | 7/2005 | Mann et al. |
| 2005/0222634 A1 * | 10/2005 | Flickinger et al. .............. 607/37 |
| 2006/0217793 A1 | 9/2006 | Costello |

OTHER PUBLICATIONS

"Implants for surgery—Active implantable medical devices—Part x: Four-pole connector system for implantable cardiac rhythm management devices", *ISO TC.150/SC 6 N*, (May 8, 2006), pp. 1-82.

"Implants for surgery—Cardiac pacemakers—Part 3: Low-profile connectors [IS-1] for implantable pacemakers", *ISO 5841-3, Second Edition*, (Oct. 15, 2000), pp. 1-19.

International Search Report from International application No. PCT/US2007/078397.

* cited by examiner

IMPLANTABLE MEDICAL DEVICE HEADER WITH OPTICAL INTERFACE

TECHNICAL FIELD

This disclosure relates generally to implantable medical device headers and, more particularly, to implantable medical device headers with an optical interface and related methods.

BACKGROUND OF THE INVENTION

Implantable medical devices (IMDs) are commonly used to provide treatment to patients. By way of example, implantable medical devices can include cardiac rhythm management devices and neurological stimulation devices, amongst others. Some types of implantable medical devices deliver electrical stimuli to a target tissue, such as in the heart or nervous system, via a lead wire ("lead") or catheter having one or more electrodes disposed in or about the target tissue. The lead is frequently connected to a pulse generator housing via an assembly commonly referred to as a header. The header serves to provide fixation of the proximal end of the lead and electrically couples the lead with the pulse generator. The pulse generator housing itself is typically hermetically sealed to prevent degradation of the components therein such as control circuitry, batteries, and the like.

Physiological information about a patient can be gathered through the use of implanted sensors. Some implanted sensors use optical techniques to gather information. For example, some implanted oxygen sensors function by shining light into a tissue of the body and then detecting and analyzing the light that is reflected back to determine blood oxygen saturation. In one approach to detecting an analyte optically, light may be generated by a light emitting diode (LED) and then detected using a photodiode. Signals generated by the photodiode representing the detected light are then processed to generate information regarding the physiological state of the patient, such as whether or not they are suffering from hypoxia. This information can then be used in further assessing a patient's condition or can be conveyed to health care professionals via an external unit.

The integration of implanted sensors with implantable medical devices, such as cardiac rhythm management devices and neurological stimulation devices, can offer various advantages. As one example, the information provided by an implanted sensor can be used to aid in the delivery of therapy from an implantable medical device. Specifically, implanted sensor information may reveal a physiological state that suggests altering the manner in which the implantable medical device delivers therapy.

However, the integration of implanted sensors with implantable medical devices also poses various challenges. For example, in the context of implanted optical sensors, one challenge is coupling both optical signals and electrical signals between leads and pulse generators in an efficient design. Accordingly, there is a need for systems and methods of efficiently integrating optical signals with implanted medical devices.

SUMMARY OF THE INVENTION

Disclosed herein, among other things, is an implantable medical device header with an optical interface. The header assembly can include a housing defining a cavity for receiving a proximal end of a lead; an electrical contact disposed along the cavity; an electrical conductor configured to electrically couple the electrical contact with the implantable medical device; and an optical conductor configured to optically couple the lead with the implantable medical device.

In an embodiment, the header assembly can include a housing defining a first cavity for receiving a proximal end of an electrical lead; and a second cavity for receiving a proximal end of an optical lead; an electrical conductor configured to electrically couple the electrical lead with the implantable medical device; and an optical conductor configured to optically couple the optical lead with the implantable medical device.

In an embodiment, the header assembly can include a housing configured to be coupled to the implantable medical device, the housing defining a lead port for receiving a proximal end of a lead, the port configured to be in electrical and optical communication with the lead; a transducer disposed within the housing, and an electrical conductor disposed within the housing. The electrical conductor can be configured to provide electrical communication between the transducer and the implantable medical device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Integrating optical signals from implanted sensors with implanted medical devices, such as cardiac rhythm management devices or neurological stimulation devices, can be advantageous for various reasons. First, the information gathered by an implanted sensor can enhance the ability of implanted medical devices to diagnose or treat problems. For example, because a patient's potassium ion concentration is relevant to cardiac arrhythmias, integrating potassium ion concentration information from an implanted sensor with an implanted cardiac rhythm management system can improve the ability of the cardiac rhythm management system to diagnose and treat cardiac rhythm problems. Second, many implanted medical devices already contain memory and/or telemetry circuitry to store and communicate information about a patient to an external monitoring device. Therefore, it can be efficient from a design perspective to pass optical signals from an implanted sensor to an implanted device that already has storage and/or telemetry functionality instead of duplicating that functionality in the implanted sensor.

One approach to integrating optical signals with an implantable medical device is to use an implantable medical device header assembly with an optical interface. In an embodiment, the invention includes a header assembly for an implantable medical device, the header assembly including a housing configured to be coupled to a pulse generator, the housing defining a first cavity for receiving a proximal end of an electrical lead, and a second cavity for receiving a proximal end of an optical lead, an electrical conductor electrically coupled to the first cavity, and an optical conductor optically coupled to the second cavity.

A lead (or catheter) is the component of an implantable system that connects the pulse generator to the target tissue, such as the heart. One issue associated with the design of leads and header assemblies has been the incompatibility of certain leads with certain header assemblies because of the lack of a consistent lead-header interface design. This issue was addressed by the adoption of industry standards specifying the configuration of the lead-header interface. The industry standards include the DF-1, VS-1, IS-1 and IS-4 standards, amongst others. The DF-1, VS-1, IS-1 and IS-4 standards include design requirements that specify the length and diameter of various portions of the cavity in the header that receives the proximal end of the lead. However, the industry standards do not include any provisions for optical connections from the lead to the header.

Embodiments of the present invention can include headers compatible with international standards (such as DF-1, VS-1, IS-1 or IS-4) that are also capable of interfacing with leads carrying optical signals. In an embodiment, the port or cavity in the header conforms to the specifications of a standard such as the DF-1, VS-1, IS-1 or IS-4 industry standard. By conforming to industry standards, some embodiments of headers in accordance with the invention can allow for backward compatibility with old leads and forward compatibility with future optically enabled and conventional leads yet to be introduced. This compatibility can offer various advantages. For example, it is well known that leads may be difficult to remove from a patient after they have been implanted for a period of time. The use of a header in accordance with an embodiment of the invention can allow a physician to choose between simply using the old leads that are already implanted or implanting new leads, such as optically enabled leads.

In an embodiment, the invention includes a header assembly for an implantable medical device, the header assembly including a housing defining a cavity for receiving a proximal end of a lead; an electrical contact disposed along the cavity; an electrical conductor configured to electrically couple the electrical contact with the implantable medical device; and an optical conductor configured to optically couple the lead with the implantable medical device.

While the transmission of optical signals to and from a medical device by way of an optically enabled header have been described with respect to the application of integrating optical sensor information with implantable medical devices, it will be appreciated that there are also other circumstances in which it may be desirable to provide an optically enabled header. By way of example, in some cases optical signals may be directly used to provide stimulation and/or therapy to a tissue and this may be facilitated by using an optically enabled header. As a further example, in some circumstances optical signals may be used in lieu of electrical signals because of the disruptive effect that electrical conductors may have on diagnostic equipment (such as some types of imaging devices). Thus, optically enabled headers may also be applied in the context of implanted medical systems that are designed for reduced interference for imaging devices. In an embodiment, the invention includes an MRI-compatible header assembly.

It will be appreciated that the transmission of optical signals between lead(s) and the pulse generator as facilitated by some embodiments of the invention can be unidirectional or bidirectional. Specifically, in some embodiments optical signals can be transmitted from the lead(s) through the header and into the pulse generator. In other embodiments, optical signals can be transmitted from the pulse generator through the header and through the lead(s). In some instances, optical signals can be transmitted both from the pulse generator through the header and through the lead(s) and from the lead(s) through the header and into the pulse generator.

Figure 1:
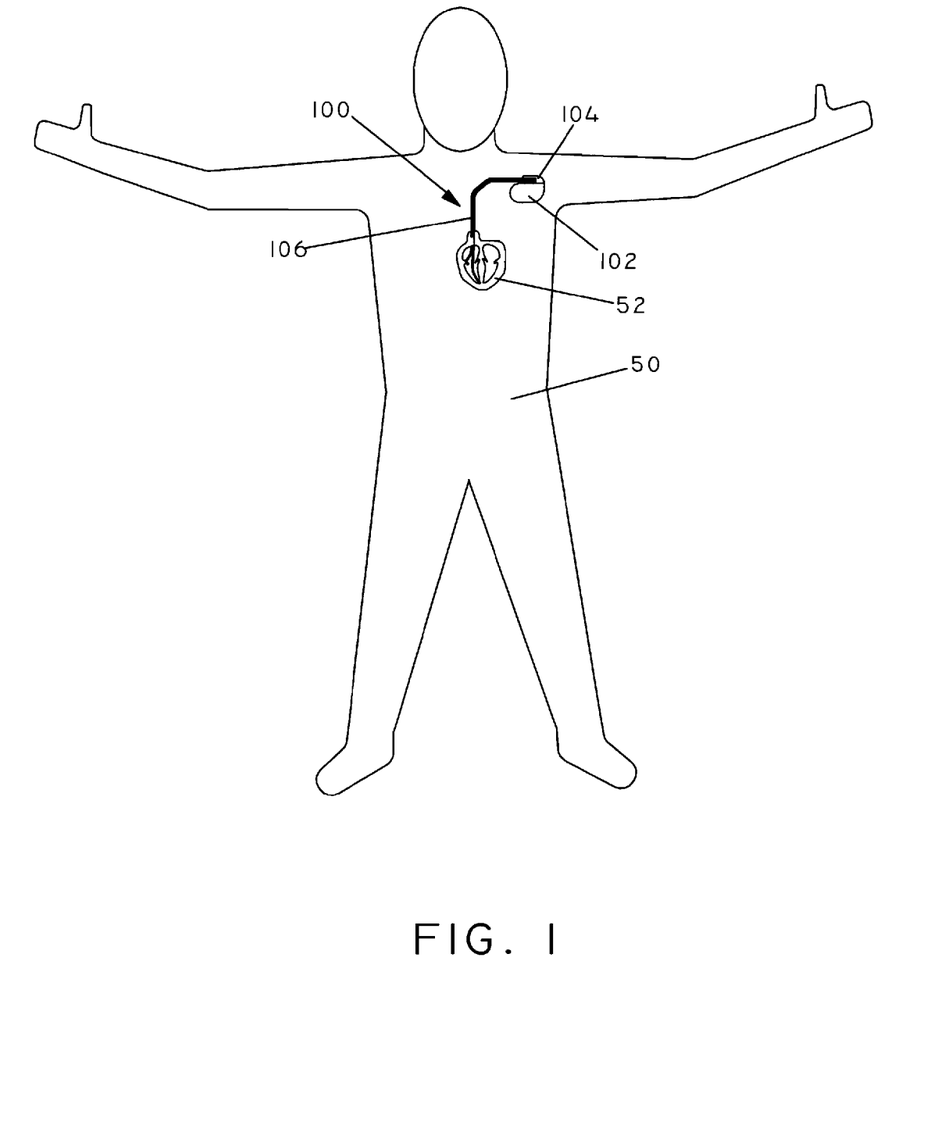
FIG. 1 is a schematic view of an implantable medical device disposed within a patient in accordance with an embodiment of the invention.

Referring now to FIG. 1, a schematic view is shown of an implantable medical system 100 in accordance with an embodiment of the invention disposed within the body 50 of a patient. The implantable medical system 100 includes a pulse generator 102, a header 104, and one or more leads 106. Depending on the configuration, the leads 106 can provide electrical and/or optical communication between the distal ends of the leads 106 and the pulse generator 102. In FIG. 1, the distal ends of the leads 106 are located in the patient's heart 52.

In various embodiments, the implantable medical device 100 can include a cardiac rhythm management device, such as a pacemaker, a cardiac resynchronization therapy (CRT) device, a remodeling control therapy (RCT) device, a cardioverter/defibrillator, or a pacemaker-cardioverter/defibrillator. In some embodiments, the implantable medical device 100 can include a neurological stimulation device. The term "pulse generator" as used herein shall refer to the part or parts of an implanted system, such as a cardiac rhythm management system or a neurological therapy system, containing the power source and circuitry for delivering pacing, electrical stimulation, and/or shock therapy. It will be appreciated that embodiments of the invention can also be used in conjunction with implantable medical devices that lack pulse generators such as monitoring devices and drug delivery devices.

Figure 2:
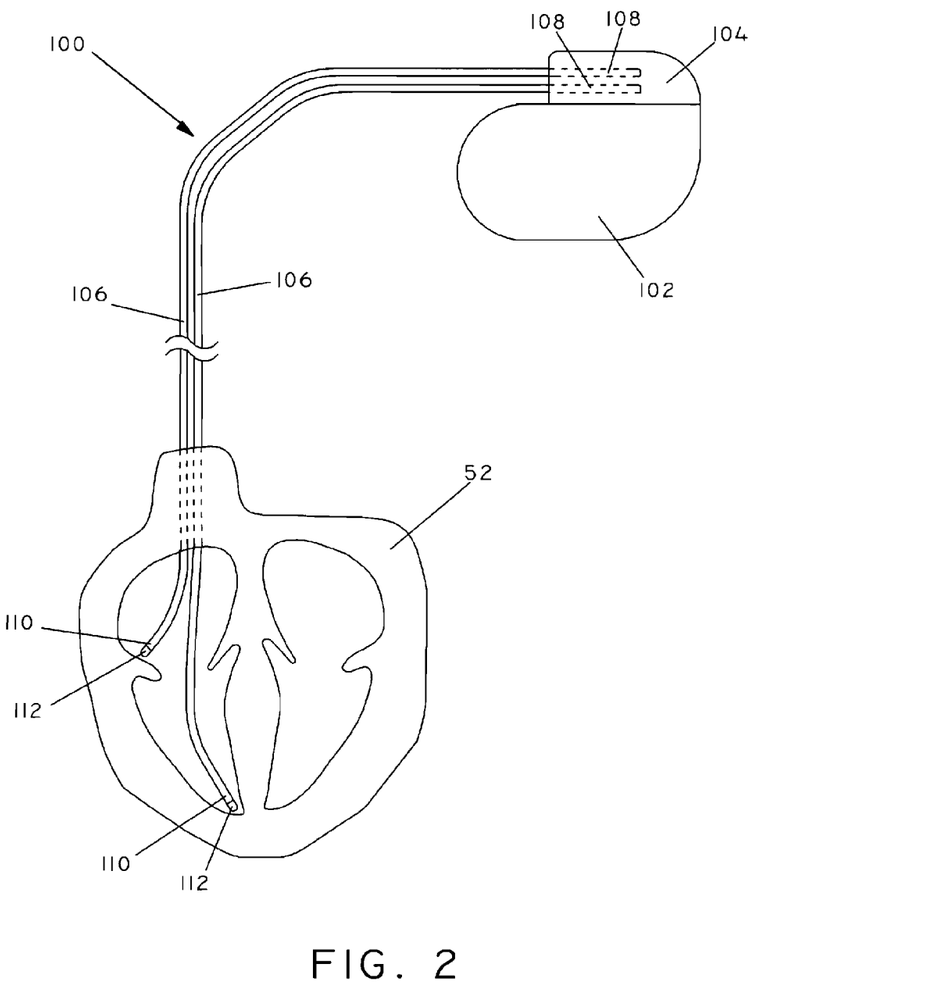
FIG. 2 is an enlarged view of the implantable medical device of FIG. 1 in conjunction with a heart.

FIG. 2 is an enlarged view of the implantable medical system 100 of FIG. 1, shown in conjunction with a heart 52. In this view, the proximal ends 108 of the leads 106 are disposed within the header 104. During the procedure of implanting the implantable medical system 100, the leads 106 are generally threaded through a major vein (typically the subclavian vein) in the upper chest and into the heart with the help of imaging devices. The leads 106 transvenously pass to the heart 52 where the distal ends 110 of the leads 106 include electrodes 112. Once the leads 106 are in the proper position, they are attached to the pulse generator 102 via the header 104. Specifically, the proximal ends of the leads 106 are inserted into ports in the header 104 and then secured in place. Typically, a set screw is used to secure the proximal ends of the leads 106 in the ports in the header 104. However, it will be appreciated that other techniques could be used to secure the proximal ends of the leads 106, such as the use of other fasteners, adhesives, or a compression type fitting.

In operation, the pulse generator 102 may generate pacing pulses or therapeutic shocks which are delivered to the heart 52 via the leads 106. In many embodiments, the leads 106 include a material that is electrically conductive in order to deliver the pacing pulses or therapeutic shocks. The leads 106 may also include, or be connected to, an optical sensor that is used to gather physiological information regarding the patient. In some embodiments, the leads 106 can include, for at least a portion of their length, an optical conductor for unidirectional or bidirectional transmission of optical signals through the leads 106. In other embodiments, separate electrical and optical leads 106 are used.

Figure 3:
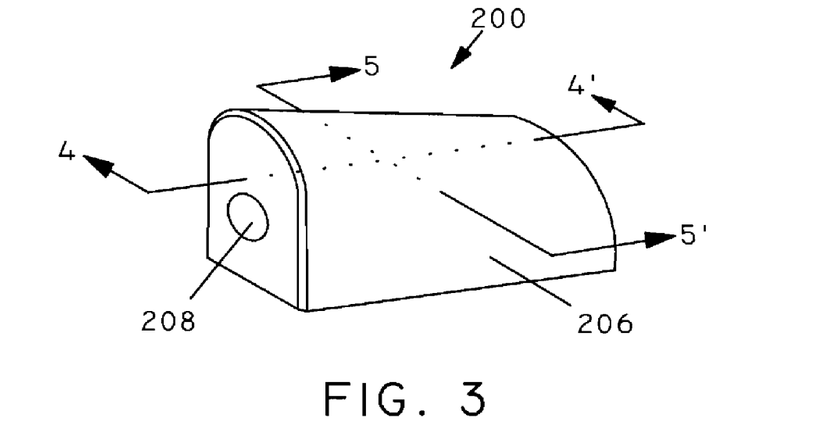
FIG. 3 is a schematic perspective view of an implantable medical device header in accordance with an embodiment of the invention.

One approach to integrating optical and electrical functionality in an implantable medical system is to use a header that can receive the proximal ends of leads that are both optically and electrically enabled. FIG. 3 is a schematic perspective view of an implantable medical device header 200 in accordance with an embodiment of the invention. The header 200 includes a housing 206 that can be configured to be coupled to a pulse generator. The housing 206 can be made of many different materials. In some embodiments, the housing 206 is made of a polymer, such as polyurethane. In some embodiments the polymer can be translucent. In an embodiment, the housing can include TECOTHANE TT-1075D available from Noveon, Inc., Cleveland, Ohio. The housing 206 defines a cavity 208 (or port) for receiving a proximal end of a lead. For simplicity, only one cavity 208 is shown in FIG. 3, however, it will be appreciated that the housing 206 can define a plurality of cavities. For example, the housing can define two, three, four, five, six, or even more cavities depending on the number of leads used.

Figure 4:
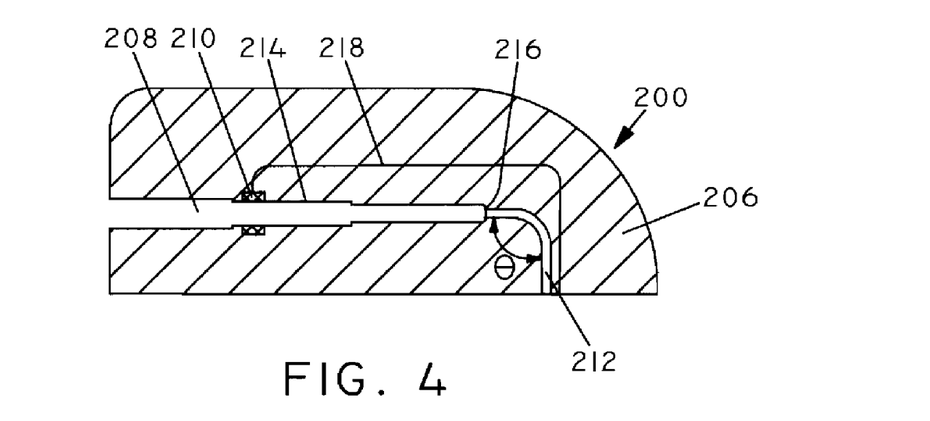
FIG. 4 is a schematic cross-sectional view of an implantable medical device header taken along line 4-4' of FIG. 3.

FIG. 4 is a schematic cross-sectional view of an implantable medical device header 200 taken along line 4-4' of FIG. 3. The cavity 208 can include a side wall 214 and an end wall 216. In some embodiments, the surfaces of the side wall 214 are substantially perpendicular to the end wall 216. An electrical contact 210 is disposed in the side wall 214 of the cavity 208. The electrical contact 210 can include, but is not limited to, conductive materials such as conductive metals including silver, gold, platinum, palladium, titanium, iridium and alloys such as MP35N (nickel-cobalt-chromium-molybdenum), platinum-iridium, and the like. An electrical conductor 218 is disposed on or within the housing 206 and is configured to electrically couple the electrical contact 210 with the pulse generator. The electrical conductor 218 can include, but is not limited to, conductive materials such as conductive metals including silver, gold, platinum, palladium, titanium, iridium and alloys such as MP35N (nickel-cobalt-chromium-molybdenum), platinum-iridium, and the like.

An optical conductor 212 is disposed within the housing 206 and configured to optically couple the end wall 216 of the cavity 208 with the pulse generator. The optical conductor 212 can include a wave guide, an optical lens (for example a gradient index (GRIN) lens), an optical window, a mirror, a light pipe, a hollow tube, a prism, or other optical components, or combinations of these components. The optical conductor 212 is configured to redirect light passing through the header by an angle $\theta$. Angle $\theta$ can include a range of angles depending on the particular configuration of the header and the pulse generator to which the header attaches. In some embodiments, angle $\theta$ can be from about 0 degrees to about 180 degrees. In other embodiments, angle $\theta$ can be from about 60 degrees to about 120 degrees. In still other embodiments, angle $\theta$ can be from about 80 to about 100 degrees. In a particular embodiment, angle $\theta$ is about 90 degrees.

Embodiments of the header can also include those wherein an optical path through the housing includes one or more free space regions wherein optical transmission occurs without the benefit of a focusing or steering element such as a lens, or the like. As such, in some embodiments, the optical path through the housing can include regions where light is transmitted through a gas, a liquid, or a vacuum.

Figure 5:
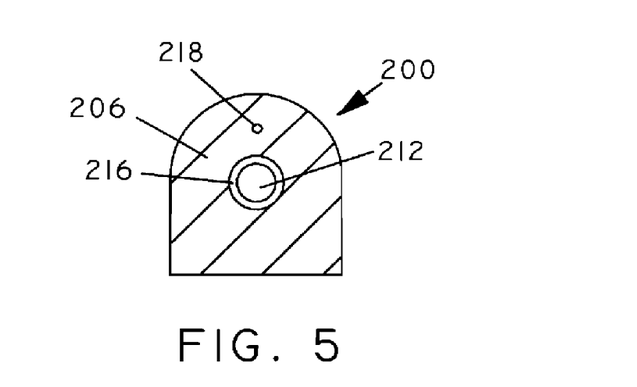
FIG. 5 is a schematic cross-sectional view of an implantable medical device header taken along line 5-5' of FIG. 3.

FIG. 5 is a schematic cross-sectional view of an implantable medical device header taken along line 5-5' of FIG. 3. In this view, the end wall 216 of the cavity 208 is circular and the optical conductor 212 is disposed in the center of the end wall 216. However, it will be appreciated that the end wall 216 can also take on other shapes such as a square or a rectangular shape. In addition, in some embodiments, the optical conductor 212 can be disposed in other positions with respect to the end wall 216 and is not limited to being disposed in the center. It will be appreciated that although the electrical conductor 218 is shown passing through the housing 206 internally in this embodiment, in other embodiments the electrical conductor 218 can be disposed on or near the surface of the housing.

Figure 6:
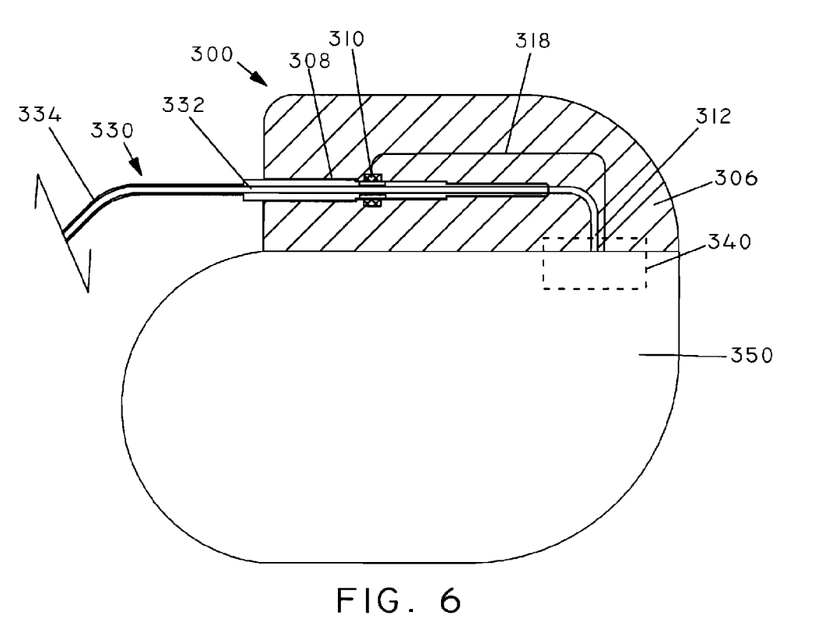
FIG. 6 is a schematic cross-sectional view of an implantable medical device header in conjunction with a lead and a pulse generator housing in accordance with an embodiment of the invention.

FIG. 6 is a schematic cross-sectional view of an implantable medical device header 300 in conjunction with a lead 330 and a pulse generator housing 350 in accordance with an embodiment of the invention. The header 300 includes a housing 306 defining a port or cavity 308 for receiving a proximal end of a lead 330. An electrical contact 310 interfaces with the cavity 308. An electrical conductor 318 is disposed within the housing 306 and electrically couples the electrical contact 310 with a pulse generator housing 350. A header optical conductor 312 is disposed within the housing 306 and configured to optically couple the cavity 308 with the pulse generator housing 350. The lead 330 can include a lead optical conductor 332 disposed within a lumen of a lead body 334. In some embodiments, the header optical conductor 312 can be continuous with the lead optical conductor 332. By way of example, the header optical conductor 312 and the lead optical conductor 332 can be a continuous piece of optical fiber passing through a conduit within the housing 306. The lead body 334 can also include a lead electrical conductor. The lead optical conductor 332 and the lead electrical conductor can be integrated, such as being disposed within a lumen of the other (co-axial), or they can be separate.

When the proximal end of the lead 330 is properly positioned within the cavity 308 of the header 300, the optical conductor 332 within the lead 330 can be in optical communication with the optical conductor 312 within the header housing 306. In addition, an electrical conductor within the lead body 334 can be in electrical communication with the electrical contact 310 within the cavity 308.

Figure 7:
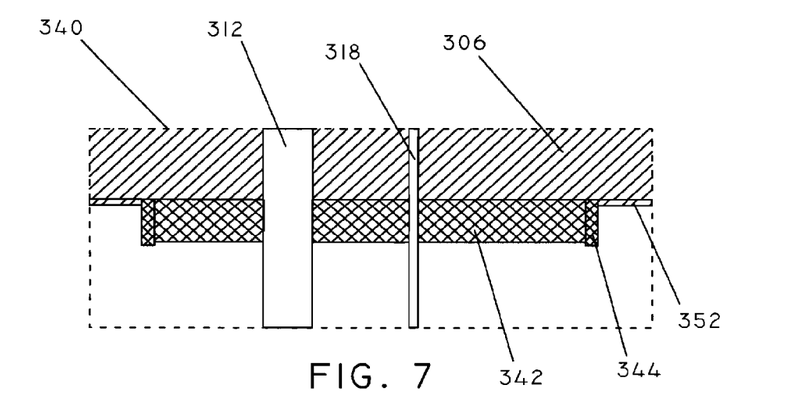
FIG. 7 is a schematic cross-sectional view of an interface between an implantable medical device header and a pulse generator.

The optical conductor 312 within the header housing 306 and the electrical conductor 318 within the header housing 306 can interface with the pulse generator housing 350 at an interface region 340. FIG. 7 shows an enlarged cross-sectional view of the interface region 340 between an implantable medical device header and a pulse generator. In this embodiment, the optical conductor 312 and the electrical conductor 318 pass from the header housing 306 and though a housing wall 352 of the pulse generator. A sealing mechanism including a sealing block 342 and a frame 344 are used to allow the optical conductor 312 and the electrical conductor 318 to enter the pulse generator while maintaining the hermeticity of the pulse generator. The optical conductor 312 and the electrical conductor 318 may be anchored into the sealing block 342 and hermetically sealed by brazing or other techniques. The sealing block 342 may include various materials such as metals, plastics, and ceramics. In an embodiment, the sealing block 342 includes alumina. The frame 344 can be welded to the housing wall 352 of the pulse generator. The frame 344 can also be made of various materials such as metals. In an embodiment, the frame 344 is made of titanium.

While the embodiment shown in FIG. 7 illustrates the optical conductor 312 passing through the sealing block 342, it will be appreciated that in other embodiments the optical conductor 312 may not pass through the sealing block 342. By way of example, in an embodiment a lens, such as a GRIN lens, may be disposed within the sealing block 342 and the optical conductor 312 may pass optical signals through the sealing block via the lens.

Figure 8:
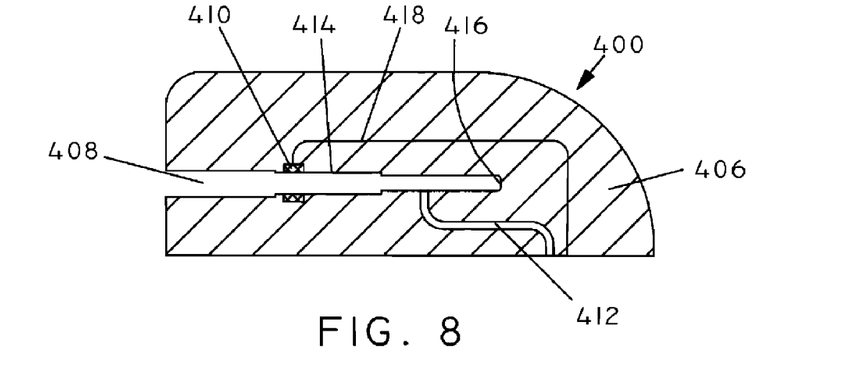
FIG. 8 is a schematic cross-sectional view of an implantable medical device header in accordance with another embodiment of the invention.

While the embodiment shown in FIG. 4 illustrates an embodiment where the optical conductor 212 is disposed within the end wall 216 of the cavity 208, it will be appreciated that the optical conductor 212 may also be configured to be disposed in the side wall 214 of the cavity. FIG. 8 is a schematic cross-sectional view of an implantable medical device header 400. A housing 406 defines a cavity 408 or port for receiving a lead. The cavity 408 can include a side wall 414 and an end wall 416. An electrical contact 410 is disposed in the side wall 414 of the cavity 408. An electrical conductor 418 is disposed within the housing 406 and is configured to electrically couple the electrical contact 410 with a pulse generator. An optical conductor 412 is disposed within the housing 406 and configured to optically couple the side wall 414 of the cavity 408 with a pulse generator. It will be appreciated that various techniques may be used to couple an optical signal within the lead with an optical conductor in the side wall of the cavity 408.

Figure 9:
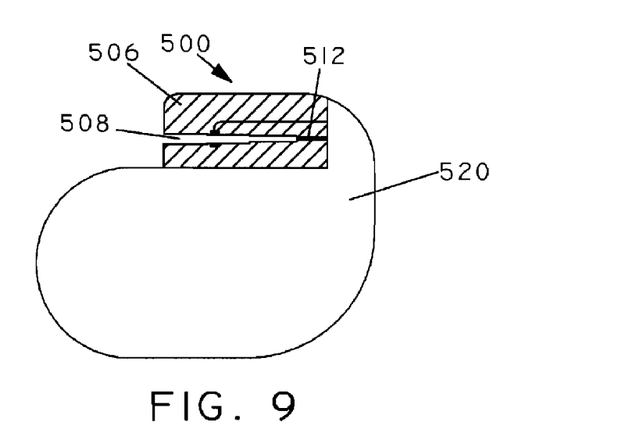
FIG. 9 is a schematic cross-sectional view of an implantable medical device header in conjunction with a pulse generator housing in accordance with another embodiment of the invention.

While the embodiment shown in FIG. 4 illustrates an optical conductor 312 configured to redirect light passing through the header by an angle θ, it will be appreciated that in some embodiments an optical conductor is used in a configuration where it does not redirect light through an angle within the header. Referring now to FIG. 9, a schematic cross-sectional view of an implantable medical device header 500 in conjunction with a pulse generator housing 520 in accordance with another embodiment of the invention is shown. The header 500 includes a housing 506 defining a port or cavity 508 for receiving a proximal end of a lead. An optical conductor 512 is disposed within the housing 506 and is configured to conduct optical signals between a lead and a pulse generator housing 520. However, in this embodiment, the optical conductor 512 does not serve to redirect the light through an angle but rather passes it straight through to the pulse generator housing 520.

Figure 10:
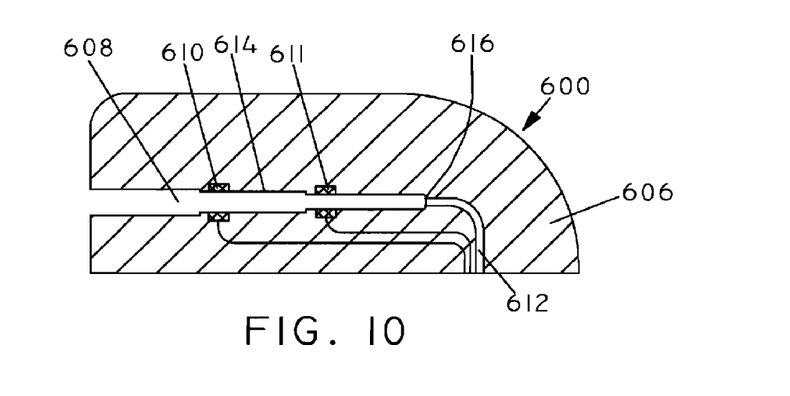
FIG. 10 is a schematic cross-sectional view of an implantable medical device header in accordance with another embodiment of the invention.

FIG. 10 is a schematic cross-sectional view of an implantable medical device header 600 in accordance with another embodiment of the invention. In this embodiment, the header 600 includes a housing 606 that defines a cavity 608 for receiving a proximal end of a lead. A first electrical contact 610 and a second electrical contact 611 are disposed in the side wall 614 of the cavity 608. By way of example, a cavity (or port) with two electrical contacts can be used to engage with a bipolar lead where one contact is configured to be in electrical communication with a tip electrode and the other is configured to be in electrical communication with a ring electrode. Alternatively, the two electrodes may be used redundantly to connect to the proximal end of a unipolar lead. An optical conductor 612 is disposed within the housing 606 and configured to optically couple the end wall 616 of the cavity 608 with the pulse generator.

Figure 11:
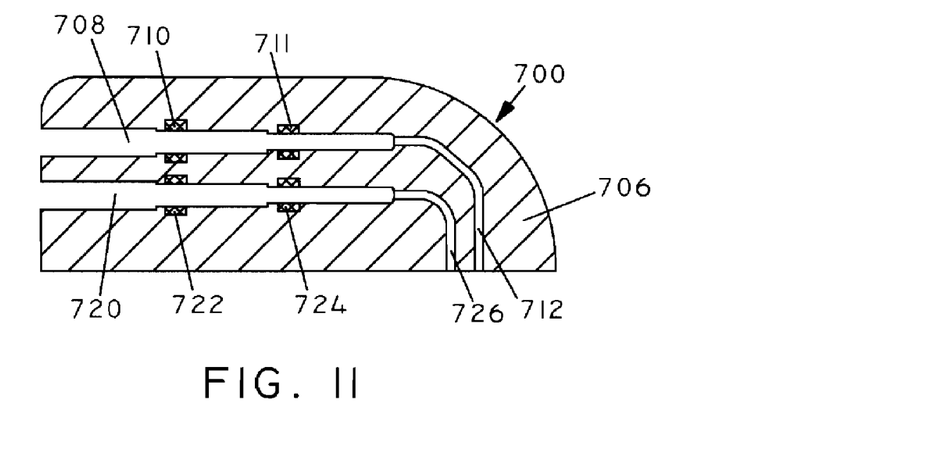
FIG. 11 is a schematic cross-sectional view of an implantable medical device header in accordance with another embodiment of the invention.

FIG. 11 is a schematic cross-sectional view of an implantable medical device header 700 in accordance with another embodiment of the invention. In this embodiment, the header 700 includes a housing 706 that defines a first cavity (or port) 708 for receiving a proximal end of a first lead or a first connector on a lead. Electrical contacts 710, 711 are disposed in the side wall of the cavity 708. A first optical conductor 712 is disposed within the housing 706 and configured to optically couple the end wall of the first cavity 708 with the pulse generator. The housing 706 also defines a second cavity (or port) 720 for receiving a proximal end of a second lead or a second connector of a bifurcated lead. Electrical contacts 722, 724 are disposed in the side wall of the cavity 720. A second optical conductor 726 is disposed within the housing 706 and configured to optically couple the end wall of the second cavity 720 with the pulse generator.

Figure 12:
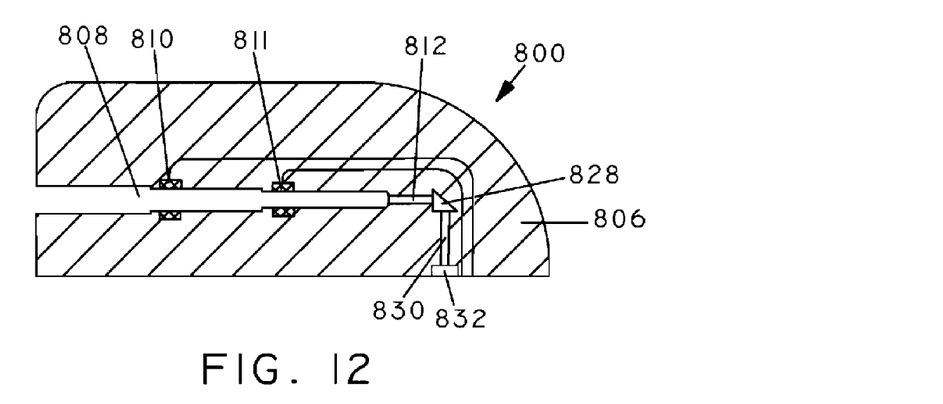
FIG. 12 is a schematic cross-sectional view of an implantable medical device header in accordance with another embodiment of the invention.

It will be appreciated that various optical components may be used in the header to conduct photonic energy from the proximal end of the lead to the pulse generator. FIG. 12 is a schematic cross-sectional view of an implantable medical device header 800 in accordance with another embodiment of the invention. In this embodiment, the header 800 includes a housing 806 that defines a cavity 808 for receiving a proximal end of a lead. A first electrical contact 810 and a second electrical contact 811 are disposed in the side wall of the cavity 808. An optical conductor 812 is disposed within the housing 806 and configured to optically couple the end wall of the cavity 808 with a prism 828 that reflects light into a second optical conductor 830 which in turn transfers the light to a lens 832. The lens 832 may serve to focus the light onto an optical window on the pulse generator. Alternately, the lens 832 itself may serve as an optical window on the pulse generator.

Figure 13:
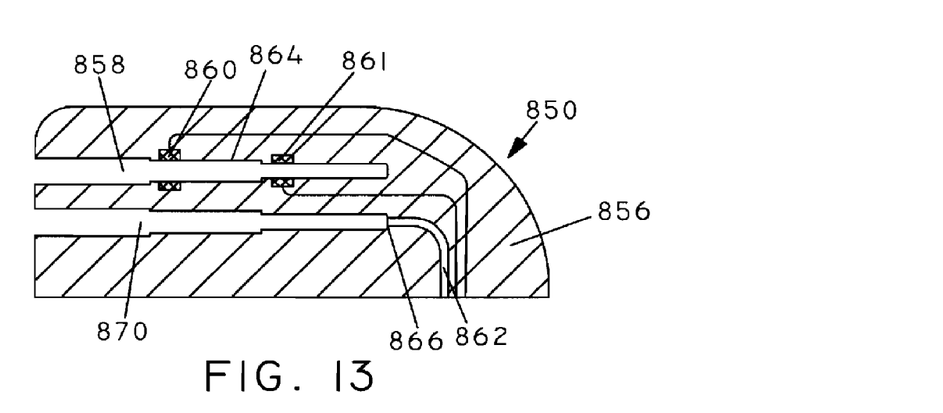
FIG. 13 is a schematic cross-sectional view of an implantable medical device header in accordance with another embodiment of the invention.

Headers in accordance with some embodiments of the invention can include ports that are optically enabled as well as those that are not optically enabled. FIG. 13 is a schematic cross-sectional view of an implantable medical device header 850 in accordance with another embodiment of the invention. In this embodiment, the header 850 includes a housing 856 that defines a first cavity 858 for receiving a proximal end of an electrical lead. A first electrical contact 860 and a second electrical contact 861 are disposed in the side wall 864 of the first cavity 858. The housing 856 also defines a second cavity 870 for receiving a proximal end of an optical lead. An optical conductor 862 is disposed within the housing 856 and is configured to optically couple the end wall 866 of the cavity 870 with a pulse generator.

In some circumstances, it may be desirable to only pass electrical conductors, such as wires, through from the exterior of the pulse generator case to the interior of the pulse generator case as opposed to passing both electrical conductors and optical conductors. This is because passing both electrical conductors and optical conductors through the case of the pulse generator may lead to increased challenges in maintaining the hermeticity of the pulse generator case. As such, in some embodiments, the header of the invention includes a transducer to convert photonic energy into electrical energy which can then be passed across the hermetic seal of the pulse generator case via an electrical conductor, such as a wire. In some embodiments, the transducer can convert electrical energy into photonic energy.

Figure 14:
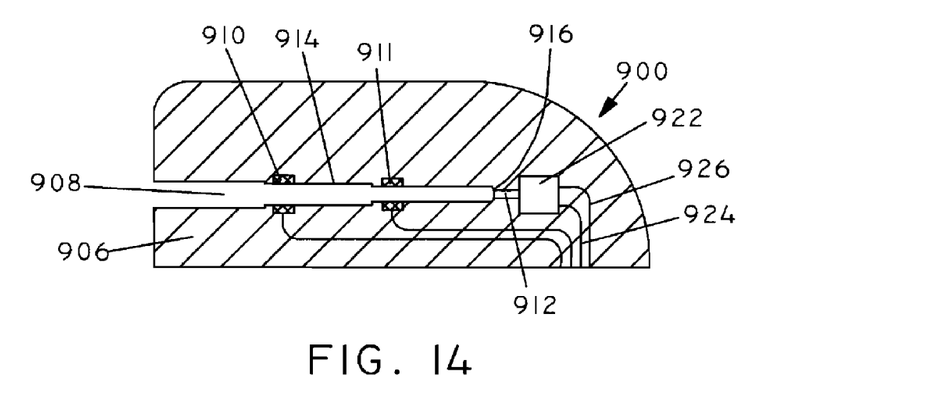
FIG. 14 is a schematic cross-sectional view of an implantable medical device header in accordance with another embodiment of the invention.

Referring now to FIG. 14, a schematic cross-sectional view of an implantable medical device header 900 in accordance with another embodiment of the invention is shown. In this embodiment, the header 900 includes a housing 906 that defines a cavity 908 for receiving a proximal end of a lead. A first electrical contact 910 and a second electrical contact 911 are disposed in the side wall 914 of the cavity 908. An optical conductor 912 is disposed within the housing 906 and is configured to optically couple the end wall 916 of the cavity 908 with a transducer 922, such as an opto-electrical transducer and/or an electro-optical transducer. The transducer 922 may include various components for the purposes of converting photonic signals into electrical signals and vice versa. By way of example, the transducer 922 may include components such as a photodiode or another type of light receptor. In addition, the transducer 922 may include components such as a light emitting diode (LED) or other type of light generator. One or more electrical conductors (924 and 926) can serve to electrically couple the transducer 922 with the pulse generator.

Figure 15:
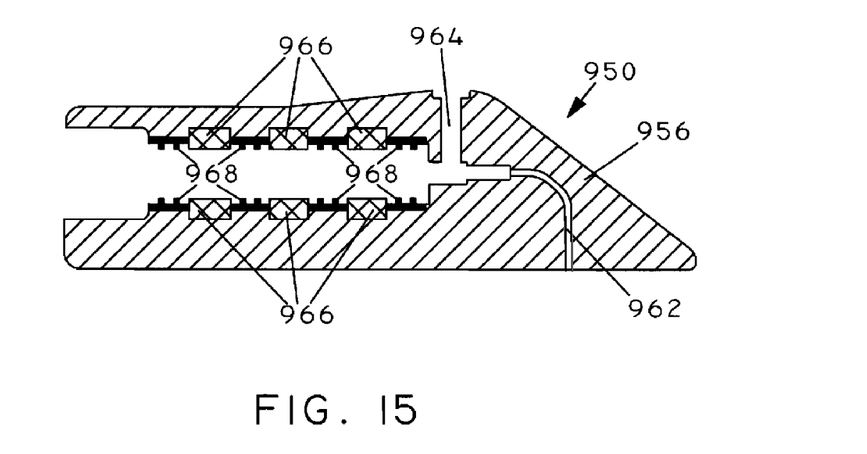
FIG. 15 is a schematic cross-sectional view of an implantable medical device header in accordance with another embodiment of the invention.

Headers in accordance with embodiments of the invention can include components to aid in the secure fixation of the proximal end of the leads to the ports in the header. Referring now to FIG. 15, a schematic cross-sectional view of an implantable medical device header 950 in accordance with another embodiment of the invention is shown. In this embodiment, the header 950 includes a housing 956 that defines a cavity for receiving a proximal end of a lead. A plurality of electrical contacts 966 are disposed in the side wall of the cavity. An optical conductor 962 is disposed within the housing 956 and is configured to optically couple the end wall of the cavity with the pulse generator. A fastening port 964 is disposed within the housing 956 and serves to facilitate the use of a fastener, such as a set screw, to secure the lead within the cavity. A plurality of sealing rings 968 are also disposed within the cavity that can engage the proximal end of the lead(s) and serve to isolate the electrical contacts 966. The sealing rings 968 can also prevent or reduce exposure of the electrical contacts and/or optical interfaces to biological fluids.

It will be appreciated that the cavity or port defined by the header housing may take on various configurations and shapes depending on the configuration and size of the lead it is designed to receive. In some embodiments, the cavities or ports defined by the header housing have physical dimensions conforming with the international standards that apply to headers such as the DF-1, VS-1, IS-1 or IS-4 standards.

Figure 16:
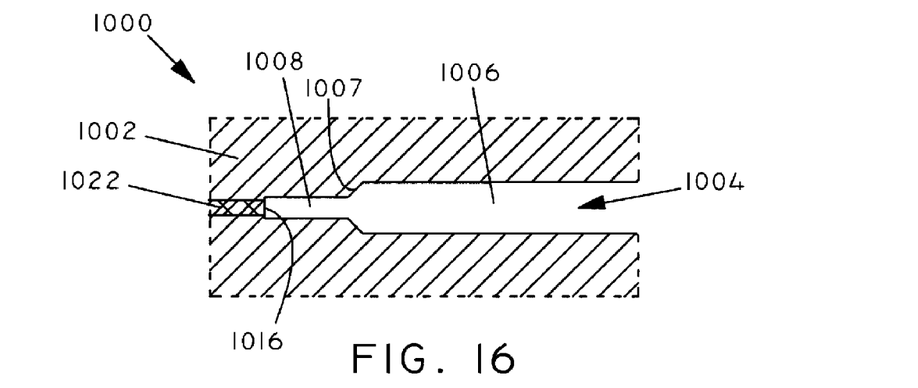
FIG. 16 is a schematic cross-sectional view of a cavity for receiving a lead in accordance with an embodiment of the invention.

Referring now to FIG. 16, a schematic cross-sectional view of a cavity or port for receiving a lead in accordance with an embodiment of the invention is shown. A header housing 1002 defines a cavity 1004 or port. The cavity 1004 has an end wall 1016 and an optical conductor 1022 in communication with the end wall 1016. The cavity 1004 includes a first region 1006, a beveled segment 1007, and a second region 1008. The first region 1006 has a diameter of approximately 3.48 mm. The first region 1006 has a length of less than or equal to about 18 mm. The second region 1008 has a diameter of approximately 1.31 mm. The second region 1008 and the beveled segment together have a length of greater than or equal to about 6.31 mm. These measurements approximate the dimensions of the DF-1 international standard (ISO 11318:2002 (E)) for a lead-header interface. In an embodiment, the header assembly of the invention includes a housing defining a cavity with physical dimensions that conform to the DF-1 international standard.

Figure 17:
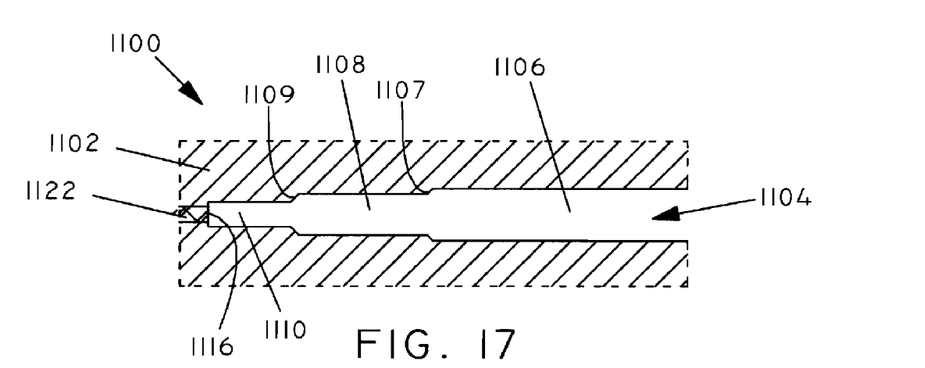
FIG. 17 is a schematic cross-sectional view of a cavity for receiving a lead in accordance with another embodiment of the invention.

Referring now to FIG. 17, a schematic cross-sectional view of a cavity or port for receiving a lead is shown. A header housing 1102 defines a cavity 1104 or port. The cavity 1104 has an end wall 1116 and an optical conductor 1122 in communication with the end wall 1116. The cavity 1104 includes a first region 1106, a first beveled segment 1107, a second region 1108, a second beveled segment 1109, and a third region 110. The first region 1106 has a diameter of approximately 3.48 mm. The first region 1106 and the first beveled segment 1107 together have a length of no more than 17 mm. The second region 1108 has a diameter of approximately 2.75 mm. The second region 1108 and the second beveled segment 1109 together have a length of approximately 9.15 mm. The third region 1110 has a length of no less than 5.46 mm. These measurements approximate the dimensions of the IS-1 international standard (ISO 5841-3:2000(E)). In an embodiment, the header assembly of the invention includes a housing defining a cavity with physical dimensions that conform to the IS-1 international standard.

Figure 18:
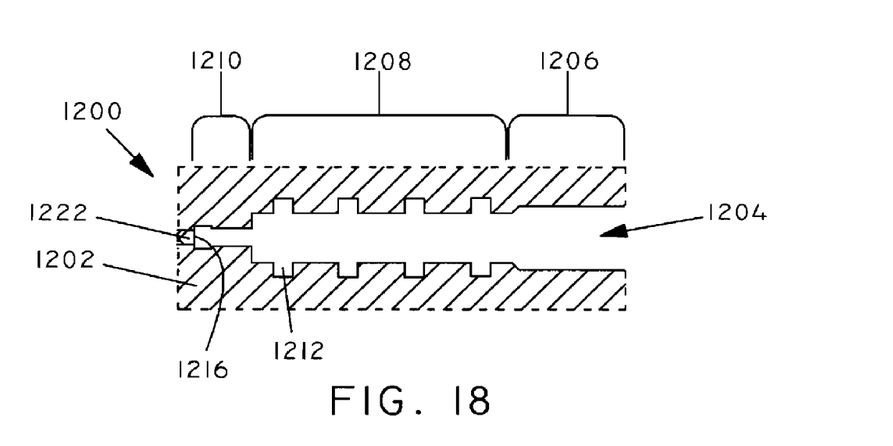
FIG. 18 is a schematic cross-sectional view of a cavity for receiving a lead in accordance with another embodiment of the invention.

Referring now to FIG. 18, a schematic cross-sectional view of a cavity or port for receiving a lead is shown. A header housing 1202 defines a cavity 1204 or port. The cavity 1204 has an end wall 1216 and an optical conductor 1222 disposed within the end wall 1216. The cavity 1204 includes a first region 1206, a second region 1208, and a third region 1210. The first region 1206 has a diameter of approximately 4.3 mm. The second region 1208 has a diameter of approximately 3.28 mm at the narrowest points. The first region 1206 and the second region 1208 have a combined length of between about 22.6 mm and about 24.6 mm. The second region 1208 has a plurality of sub-segments 1212 with a larger diameter into which sealing devices, such as sealing rings, can be disposed. The third region 1210 has a diameter of approximately 1.43 mm at its largest point. These measurements approximate the measurements according to the soon-to-be-released IS-4 international standard. In an embodiment, the header assembly of the invention includes a housing defining a cavity with physical dimensions that conform to the IS-4 international standard.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An assembly configured for an implantable medical device comprising: a hermetically sealed pulse generator; and a header assembly configured to couple a lead with the hermetically sealed pulse generator, the header assembly comprising; a housing defining a cavity configured for receiving a proximal end of the lead, the cavity bounded by a side wall and an end wall, the housing attached to the outside of the hermetically sealed pulse generator; an electrical contact disposed in the side wall of the cavity; an electrical conductor configured to electrically couple the electrical contact with the implantable medical device; and an optical conductor configured to optically couple the end wall of the cavity with the implantable medical device.

2. The assembly of claim 1, the end wall of the cavity comprising peripheral edges and a center point equidistant from the peripheral edges, the optical conductor disposed on the center point of the end wall of the cavity.

3. The assembly of claim 1, the electrical contact disposed in the side wall of the cavity.

4. The assembly of claim 1, the optical conductor comprising a waveguide.

5. The assembly of claim 4, the waveguide comprising an optical fiber.

6. The assembly of claim 1, the optical conductor comprising an optical lens.

7. The assembly of claim 6, the optical lens comprising a GRIN lens.

8. The assembly of claim 1, the optical conductor comprising a mirror.

9. The assembly of claim 1, the optical conductor comprising a prism.

10. The assembly of claim 1, further comprising a second electrical contact disposed along the cavity and a second electrical conductor configured to electrically couple the second electrical contact with the implantable medical device.

11. The assembly of claim 1, the electrical conductor welded to the electrical contact.

12. The assembly of claim 1, the optical conductor configured to redirect light passing through the header assembly by about 0 degrees to about 180 degrees.

13. The assembly of claim 1, the optical conductor configured to redirect light passing through the header assembly by about 90 degrees.

14. The assembly of claim 1, the housing comprising a translucent polymer.

15. An implantable medical device comprising: a hermetically sealed pulse generator; and a header assembly configured to couple a lead with the hermetically sealed pulse generator, the header assembly comprising a housing defining a cavity configured for receiving a proximal end of a lead, the cavity bounded by a side wall and an end wall, the housing attached to the outside of the hermetically sealed pulse generator; an electrical contact disposed in the side wall of the cavity; an electrical conductor configured to electrically couple the electrical contact with the implantable medical device; and an optical conductor configured to optically couple the end wall of the cavity with the implantable medical device, the optical conductor configure to redirect light passing through the header assembly by an angle from 60 degrees to about 120 degrees and further configured to optically couple the end wall of the cavity with the implantable medical device.

16. The implantable medical device of claim 15, the end wall of the cavity comprising peripheral edges and a center point equidistant from the peripheral edges, the optical conductor disposed on the center point of the end wall of the cavity.

* * * * *